(12) United States Patent
Smidt et al.

(10) Patent No.: US 8,461,390 B2
(45) Date of Patent: Jun. 11, 2013

(54) METHOD FOR PRODUCING SUBSTITUTED BIPHENYLS

(75) Inventors: Sebastian Peer Smidt, Oftersheim (DE); Volker Maywald, Ludwigshafen (DE); Kathrin Wissel-Stoll, Ludwigshafen (DE); Joachim Schmidt-Leithoff, Mannheim (DE); Ansgar Gereon Altenhoff, Heidelberg (DE); Michael Keil, Freinsheim (DE)

(73) Assignee: BASF SE, Ludwighsafen (DE)

( * ) Notice: Subject to any disclaimer, the term of this patent is extended or adjusted under 35 U.S.C. 154(b) by 161 days.

(21) Appl. No.: 13/001,070

(22) PCT Filed: Jun. 22, 2009

(86) PCT No.: PCT/EP2009/057719
§ 371 (c)(1),
(2), (4) Date: Dec. 23, 2010

(87) PCT Pub. No.: WO2009/156359
PCT Pub. Date: Dec. 30, 2009

(65) Prior Publication Data
US 2011/0105766 A1    May 5, 2011

(30) Foreign Application Priority Data

Jun. 25, 2008 (EP) .................................. 08158963

(51) Int. Cl.
*C07C 205/06* (2006.01)

(52) U.S. Cl.
USPC ........................................................ 564/442

(58) Field of Classification Search
None
See application file for complete search history.

(56) References Cited

U.S. PATENT DOCUMENTS

| 6,087,542 A | 7/2000 | Eicken et al. |
| 7,772,446 B2 | 8/2010 | Engel et al. |
| 2008/0183021 A1 | 7/2008 | Engel et al. |

FOREIGN PATENT DOCUMENTS

| CN | 101050157 | 10/2007 |
| DE | 4340490 | 6/1994 |
| WO | WO 97/33846 | 9/1997 |
| WO | WO 98/16486 | 4/1998 |
| WO | WO 2006/092429 | 9/2006 |

OTHER PUBLICATIONS

Hinkel et al, Journal of Chemical Society (1928), 2786-91.*
European Search Report from corresponding prior application EP 08158963.2 filed Jun. 25, 2008.
Bellavita et al., Gazetta Chimica Italiana, 1937, p. 574-576, vol. 67, Search Report.

(Continued)

*Primary Examiner* — Kamal Saeed
(74) *Attorney, Agent, or Firm* — Brinks Hofer Gilson & Lione

(57) ABSTRACT

A process for preparing substituted biphenyls of the formula I

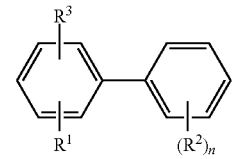

where $R^1$=nitro or amino,
$R^2$=cyano, halogen, $C_1$-$C_4$-haloalkyl, $C_1$-$C_4$-haloalkoxy or $C_1$-$C_4$-haloalkylthio,
n=from 0 to 3, and $R^3$=hydrogen, cyano or halogen,
which comprises reacting a halobenzene of the formula II

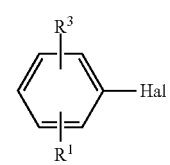

in which Hal is chlorine or bromine,
in the presence of a base and of a palladium catalyst which consists of palladium and a bidentate phosphorus ligand of the formula III

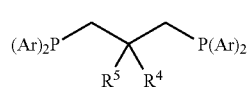

where Ar is phenyl which is substituted if desired and $R^4$ and $R^5$ are each $C_1$-$C_8$-alkyl or $C_3$-$C_6$-cycloalkyl or together form a 2- to 7-membered bridge which may, if desired, bear a $C_1$-$C_6$-alkyl substituent,
in a solvent or diluent, with a phenylboronic acid IVa

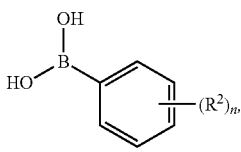

a diphenylborinic acid IVb

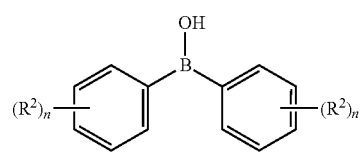

or a mixture of IVa and IVb.

1 Claim, No Drawings

OTHER PUBLICATIONS

Cai, Mingzhong, et al. "MCM-41-supported bidentate phosphine palladium(0) complex as an efficient catalyst for the heterogenous Suzuki reaction", Journal of Molecular Catalysis A: Chemical, 2007, p. 82-86, vol. 268, Search Report.

Hinkel, Leonard Eric, et al., "CLXXIX—Conversion of Hydroaromatic into Aromatic Compounds. Part IV. The Influence of Nitro-group in Nitrophenyldihydroresorcinols", Journal of the Chemical Society, 1930, p. 1387-1390, Search Report.

Hinkel, Leonard Eric, et al., "CCCLCVIII—Conversion of Hydroaromatic into Aromatic Compounds. Part III. 3:5-dichloro-1-phenyl-$\Delta^{2:4}$cyclohexadiene and its behavior with chlorine", Journal of the Chemical Society, 1928, p. 2786-2791, Search Report.

Mitchell, M. B. et al., "Coupling of Heteroaryl Chlorides with Arylboronic Acids in the Presence of [1,4-Bis-(diphenylphosphine) Butane]palladium(II) Dichloride", Tetrahedron Letters, 1991, p. 2273-2276, vol. 32, No. 20, Search Report.

Shen, Wang, "Palladium Catalyzed Coupling of Aryl Chlorides with Arylboronic Acids", Tetrahedron Letters, 1997, p. 5575-5578, vol. 38, No. 32, Search Report.

Williams, D.B.G., et al., "P-alkene bidentate ligands: an unusual ligand effect in Pd-catalysed Suzuki reactions", Tetrahedron, 2007, p. 1624-1629, vol. 63, Search Report.

* cited by examiner

METHOD FOR PRODUCING SUBSTITUTED BIPHENYLS

This application is a National Stage application of International Application No. PCT/EP2009/057719 filed Jun. 22, 2009, the entire contents of which is hereby incorporated herein by reference. This application also claims priority under 35 U.S.C. §119 to European Patent Application No. 08158963.2, filed Jun. 25, 2008, the entire contents of which is hereby incorporated herein by reference.

The present invention relates to a process for preparing substituted biphenyls of the formula I

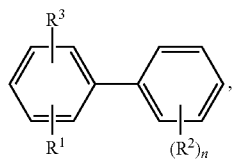

in which the substituents are each defined as follows:

$R^1$ is nitro or amino, $R^2$ is cyano, halogen, $C_1$-$C_4$-haloalkyl, $C_1$-$C_4$-haloalkoxy or $C_1$-$C_4$-haloalkylthio, n is 0, 1, 2 or 3, where, in the case that n=2 or 3, the $R^2$ radicals may have identical or different definitions, $R^3$ hydrogen, cyano or halogen, which comprises reacting a halobenzene of the formula II

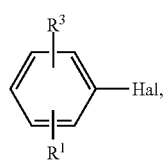

in which Hal is chlorine or bromine and $R^1$ and $R^3$ are each as defined above, in the presence of a base and of a palladium catalyst which consists of palladium and a bidentate phosphorus ligand of the formula III

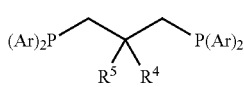

where Ar is phenyl which may bear from one to three substituents selected from the group consisting of methyl, methoxy, fluorine and chlorine, and $R^4$ and $R^5$ are each $C_1$-$C_8$-alkyl or $C_3$-$C_6$-cycloalkyl, or $R^4$ and $R^5$ together form a 2- to 7-membered bridge which may, if desired, bear a $C_1$-$C_6$-alkyl substituent, in a solvent or diluent, with a phenylboronic acid IVa

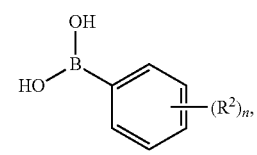

a diphenylborinic acid IVb

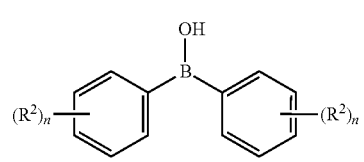

or a mixture of IVa and IVb, in which $R^2$ and n are each as defined as above.

Palladium-catalyzed couplings of chloroaromatics with aromatic boronic acids and borinic acids are known per se. For example, the coupling of 2-nitrochlorobenzene with halogen-substituted aromatic boronic acids to give the correspondingly substituted nitrobiphenyls is described in WO 97/33846. Triphenylphosphine is the most commonly used ligand for palladium in such coupling reactions. However, the use of triphenylphosphine as a ligand harbors the risk that the aromatic boronic and borinic acids used as coupling partners are protodeboronated to a greater degree and the aromatic compounds unsubstituted at this position are formed as undesired by-products. This is also true when triphenylphosphine is used in a significant molar excess based on the palladium source to improve the selectivity and yield.

It has now been found that the palladium-catalyzed reaction of chloroaromatics with halogen-substituted aromatic boronic and borinic acids in the case of use of the bidentate 1,3-bis(diphenylphosphinyl)propane (dppp) ligand proceeds with a very much poorer yield than with triphenylphosphine (see example 2b compared to 2a). When, however, a bidentate ligand slightly modified by further substituents in the alkyl chain is used, for example 1,3-bis(diphenylphosphinyl)-2,2-dimethylpropane or 1,3-bis(diphenylphosphinyl)-2-ethyl-2-butylpropane, the desired coupling products are surprisingly achieved in very good yields, and simultaneously only a very low level of protodeboronated by-products:

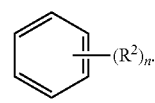

A further advantage in the case of use of these latter ligands is that both the required amount of the palladium source and the amount of the ligand can be reduced significantly compared to the method with triphenylphosphine. Since the palladium compounds used are generally very expensive, this means of reducing the use of palladium is of great economic value.

In the literature there have to date only been infrequent reports about the use of bidentate bisphosphine ligands in coupling reactions. WO 98/16486 reports the use of lipophilic aliphatic bisphosphines in reactions of simple chloroaromatics, but without proof by example.

DE-A 4340490 teaches the use of 1,2-bis(dicyclohexylphosphinyl)ethane and 1,2-bis(diethylphosphinyl)ethane in coupling reactions. Good results were achieved here with electron-rich chloroaromatics but not with aromatics which bear electron-withdrawing substituents such as fluorine or trifluoromethyl.

However, the use of completely aliphatically substituted phosphines is generally very limited, since these phosphines are very air-sensitive and some are pyrophoric.

It was therefore an object of the present invention to provide an economically viable process, which can be implemented technically on the industrial scale, for regioselective preparation of substituted biphenyls, which works with a reduced palladium catalyst concentration.

The process defined at the outset overcomes the detailed disadvantages of the prior art.

The substituted biphenyls I prepared by the present process preferably have the following substituents:

$R^1$ is nitro or amino, more preferably nitro;
$R^2$ is cyano, fluorine, chlorine, bromine, trifluoromethyl, trifluoromethoxy or trifluoromethylthio, more preferably fluorine, chlorine or trifluoromethylthio, most preferably fluorine or chlorine;
n is 2 or 3, more preferably 3;
$R^3$ is hydrogen or halogen, especially hydrogen or fluorine.

Very particular preference is given to the preparation of 3,4,5-trifluoro-2'-nitrobiphenyl.

The homogeneously catalyzed Suzuki biaryl cross-coupling which follows is performed preferably according to the following scheme:

The starting materials are preferably phenylboronic acids of the formula IVa or diphenylborinic acids of the formula IVb or mixtures thereof, in which $R^2$ and n are each as defined above.

Very particular preference is given to 3,4,5-trifluorophenylboronic acid and di(3,4,5-trifluorophenyl)borinic acid as starting compounds (IVa and IVb).

Preference is given to proceeding from compounds (II), which bear a single nitro or amino group, especially 2-nitrochlorobenzene or 2-aminochlorobenzene or 2-aminobromobenzene.

Compound II, based on the phenylboronic acid IVa or the diphenylborinic acid IVb, is normally used in an approximately equimolar amount, preferably with an excess up to about 30 mol %. In the calculation of the molar ratios and excesses, it should be considered that the diphenylborinic acid IVb, used in pure form or as a mixture with IVa, can transfer two phenyl radicals.

The bases used are preferably alkali metal hydroxides, alkaline earth metal hydroxides, alkali metal carbonates, alkaline earth metal carbonates, alkali metal hydrogen-carbonates, alkali metal acetates, alkaline earth metal acetates, alkali metal alkoxides and alkaline earth metal alkoxides, in a mixture and especially individually.

Particularly preferred bases are alkali metal hydroxides, alkaline earth metal hydroxides, alkali metal carbonates, alkaline earth metal carbonates and alkali metal hydrogencarbonates.

Especially preferred bases are alkali metal hydroxides, e.g. sodium hydroxide, potassium hydroxide and lithium hydroxide, and also alkali metal carbonates and alkali metal hydrogencarbonates, e.g. lithium carbonate, sodium carbonate and potassium carbonate.

However, the bases used may also be organic bases, e.g. tertiary amines. Preference is given to using, for example, triethylamine or dimethylcyclohexylamine.

The base is used preferably with a proportion of from 100 to 500 mol %, more preferably from 150 to 400 mol %, based on the phenylboronic acid IVa or the diphenylborinic acid IVb.

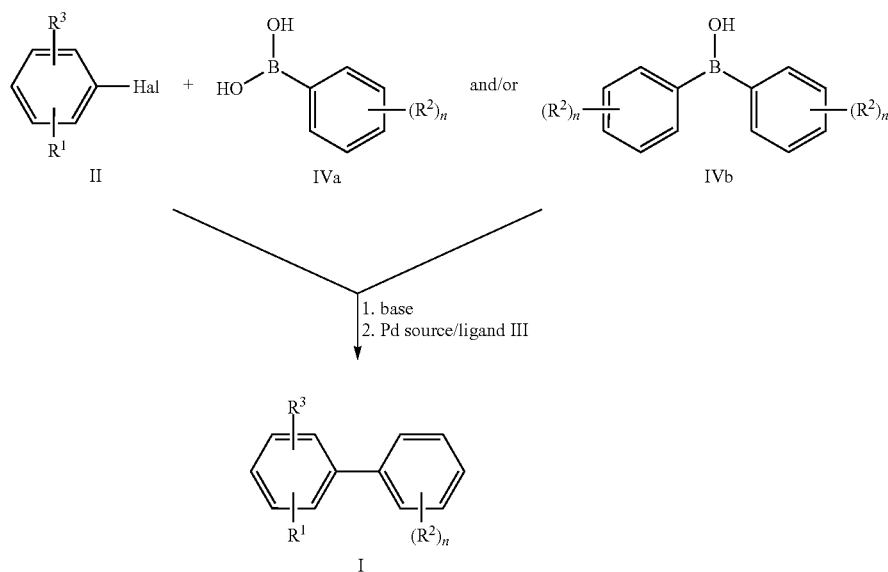

Suitable palladium sources are, for example, palladium(II) salts, such as palladium(II) chloride or palladium(II) acetate or aqueous solutions thereof, and also bisacetonitrilepalladium(II) chloride or palladium complexes with Pd in the 0 oxidation state.

Particular preference is given to using palladium(II) chloride.

Suitable bidentate phosphorus ligands substituted in the alkyl chain and the preparation thereof are known from the prior application EP 08154184.9.

Preference is given to 1,3-bis(diphenylphosphinyl)propanes III having unsubstituted phenyl rings, especially those in which $R^4$ is $C_1$-$C_6$-alkyl such as methyl, ethyl, 1-methylethyl, n-butyl, 1-methylpropyl, 2-methylpropyl, n-pentyl, 1-methylbutyl, 2-methylbutyl, 3-methylbutyl, n-hexyl, 1-methylpentyl, 2-methylpentyl, 3-methylpentyl and 4-methylpentyl, or cyclopropyl and $R^5$ is $C_1$-$C_6$-alkyl such as methyl, ethyl, 1-methylethyl, n-butyl, 1-methylpropyl, 2-methylpropyl, n-pentyl, 1-methylbutyl, 2-methylbutyl, 3-methylbutyl, n-hexyl, 1-methylpentyl, 2-methylpentyl, 3-methylpentyl and 4-methylpentyl, or in which $R^4$+$R^5$ together are an ethane-1,2-diyl, propane-1,3-diyl, butane-1,4-diyl or pentane-1,5-diyl chain.

Particularly preferred phosphorus ligands III are 1,3-bis(diphenylphosphinyl)-2-methylpropane, 1,3-bis(diphenylphosphinyl)-2,2-dimethylpropane, 1,3-bis(diphenylphosphinyl)-2-methyl-2-ethylpropane, 1,3-bis(diphenylphosphinyl)-2,2-diethylpropane 1,3-bis(diphenylphosphinyl)-2-methyl-2-propylpropane, 1,3-bis(diphenylphosphinyl)-2-ethyl-2-propylpropane, 1,3-bis(diphenylphosphinyl)-2,2-dipropylpropane, 1,3-bis(diphenylphosphinyl)-2-methyl-2-butylpropane, 1,3-bis(diphenylphosphinyl)-2-ethyl-2-butylpropane, 1,3-bis(diphenylphosphinyl)-2-propyl-2-butylpropane, 1,3-bis(diphenylphosphinyl)-2,2-dibutylpropane, 1,3-bis(diphenylphosphinyl)-2-methyl-2-cyclopropylpropane, 1,3-bis(diphenylphosphinyl)-2-methyl-2-cyclobutylpropane, 1,3-bis(diphenylphosphinyl)-2-methyl-2-cyclopentylpropane, 1,3-bis(diphenylphosphinyl)-2-methyl-2-cyclohexylpropane, 1,1-bis(diphenylphosphinyl)cyclopropane, 1,1-bis(diphenylphosphinyl)cyclobutane, 1,1-bis(diphenylphosphinyl)cyclopentane, 1,1-bis(diphenylphosphinyl)cyclohexane, especially 1,3-bis(diphenylphosphinyl)-2,2-dimethylpropane and 1,3-bis(diphenylphosphinyl)-2-ethyl-2-butylpropane.

The reactivity of the complex ligands can be enhanced by adding a quaternary ammonium salt such as tetra-n-butylammonium bromide (TBAB) (cf., for example, D. Zim et al., Tetrahedron Lett. 2000, 41, 8199).

In general, from 0.5 to 5 molar equivalents of the aforementioned complex ligands, especially 1,3-bis(diphenylphosphinyl)-2,2-dimethylpropane and 1,3-bis(diphenylphosphinyl)-2-ethyl-2-butylpropane, are combined with one equivalent of the palladium(II) salt. Particular preference is given to the use of one molar equivalent of complex ligand, based on the palladium(II) salt.

The palladium source is used in the process according to the invention at a low proportion of from 0.001 to 5.0 mol %, preferably from 0.1 to 1.0 mol %, especially from 0.1 to 0.5 mol %, based on the compound IVa or IVb.

Organic solvents suitable for the process according to the invention are ethers such as dimethoxyethane, diethylene glycol dimethyl ether, tetrahydrofuran, 2-methyltetrahydrofuran, 3-methyltetrahydrofuran, dioxane, tert-butyl methyl ether and tert-butyl ethyl ether, hydrocarbons such as n-hexane, n-heptane, heptane isomer mixtures, cyclohexane, petroleum ether, benzene, toluene and xylene, alcohols such as methanol, ethanol, 1-propanol, 2-propanol, ethylene glycol, 1-butanol, 2-butanol and tert-butanol, ketones such as acetone, ethyl methyl ketone and isobutyl methyl ketone, amides such as dimethylformamide, dimethylacetamide and N-methylpyrrolidone, and dimethyl sulfoxide, in each case individually or in a mixture.

Preferred solvents are ethers such as dimethoxyethane, tetrahydrofuran, 2-methyltetrahydrofuran, 3-methyltetrahydrofuran and dioxane, hydrocarbons such as cyclohexane, toluene and xylene, alcohols such as ethanol, 1-propanol, 2-propanol, 1-butanol and tert-butanol, in each case individually or in a mixture.

In a particularly preferred variant, in the process according to the invention, water, one or more water-insoluble and one or more water-soluble solvents are used, for example mixtures of water and dioxane or water and tetrahydrofuran or water, dioxane and ethanol or water, tetrahydrofuran and methanol or water, toluene and tetrahydrofuran, preferably water and tetrahydrofuran or water, tetrahydrofuran and methanol. Preference is given to performing the reaction in water and tetrahydrofuran.

The total amount of solvent is normally from 3000 to 100 and preferably from 2000 to 150 g per mole of the compound II.

Appropriately, to perform the process, the compound II, the phenylboronic acid IVa or the diphenylborinic acid IVb, or a mixture of the two, the base and the catalytic amount of the palladium source are added to a mixture of water and one or more inert organic solvents, and stirred at a temperature of from 50° C. to 140° C., preferably from 70° C. to 110° C., more preferably from 90° C. to 110° C., for a period of from 1 to 50, and preferably from 2 to 24 hours.

According to the solvent and temperature used, a pressure of from 1 bar to 6 bar, or preferably from 1 bar to 4 bar is established.

The performance can be effected in customary apparatus suitable for such processes.

After the reaction has ended, the palladium catalyst obtained in solid form can be removed, for example by filtration, and the crude product can be freed of the solvent or the solvents.

Subsequently, it is possible to purify further by methods which are known to those skilled in the art and are appropriate to the particular product, for example by recrystallization, distillation, sublimation, zone melting, melt crystallization or chromatography.

The process according to the invention affords the compounds I in very high up to quantitative yields coupled with very good purity.

The halobenzenes II are known or can be prepared by processes known per se.

The phenylboronic acids IVa and the diphenylborinic acids IVb are likewise known or can be prepared in a manner known per se (cf., for example, WO 2006/092429).

The substituted biphenyls I where $R^1$=nitro (biphenyls Ia) obtainable by the process according to the invention, for example 3,4-difluoro-2'-nitrobiphenyl, 2,4-dichloro-2'-nitrobiphenyl, 3,4-dichloro-2'-nitrobiphenyl and 3,4,5-trifluoro-2'-nitrobiphenyl, can be converted in a manner known per se by means of hydrogenation to the correspondingly substituted biphenyls I where $R^1$=amino (biphenyls Ib). The substituted biphenyls Ib are in turn important intermediates for crop protection active ingredients, for example fungicidally active pyrazolecarboxamides V (cf., for example, EP-A 589301 or WO 2006087343):

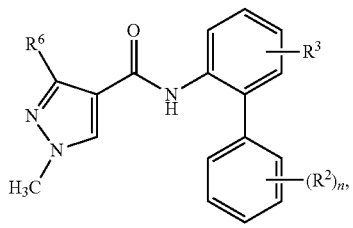

V where $R^6$ is methyl or halomethyl such as difluoromethyl or trifluoromethyl.

PREPARATION EXAMPLE

Synthesis of 3,4,5-trifluoro-2'-nitrobiphenyl a) Preparation of 3,4,5-trifluorophenylboronic acid A nitrogen- or argon-inertized reactor was initially charged with 83.2 g (3.42 mol) of magnesium turnings and then 1646.2 g of dry, unstabilized tetrahydrofuran were added. 30 g (0.14 mol) of 3,4,5-trifluorobromobenzene were added dropwise at 25° C. with stirring and the startup of the Grignard reaction was awaited. The startup of the Grignard reaction was perceptible by a spontaneous temperature increase to approx. 32° C. Subsequently, 571.9 g (2.71 mol) of further 3,4,5-trifluorobromobenzene were metered in at 25-35° C. within 5 h. To complete the reaction, the mixture was stirred at 25-30° C. for a further 2 h. A 2nd reactor was initially charged with a solution of 328.0 g (3.16 mol) of trimethyl borate and 452 g of dry, unstabilized tetrahydrofuran, which were precooled to −5° C. Thereafter, the Grignard solution was metered in from the 1st reactor within 2.5 h. The excess magnesium remained in the 1st reactor. After the metered addition had ended, the mixture was stirred at 20-25° C. for another 2 h. For hydrolysis, 1326.1 g (2.76 mol) of 7.6% hydrochloric acid were then metered in at 25° C., after which the mixture was stirred at 25° C. for another 1 h. The mixture was heated to 50° C. and the phases were separated. Thereafter, the organic phase was re-extracted with 603.9 g of water at 50° C. and the washing water phase was removed again. Subsequently, the organic phase was concentrated by distilling off a tetrahydrofuran/water mixture. This afforded 1032.6 (82%) of a 40% solution of 3,4,5-trifluorophenylboronic acid in tetrahydrofuran, which was used directly for the subsequent reactions.

b) Preparation of 3,4,5-trifluoro-2'-nitrobiphenyl by Suzuki coupling of 3,4,5-trifluorophenylboronic acid with 2-nitrochlorobenzene A well-inertized pressure vessel was initially charged with a mixture of 49.6 g (0.113 mol) of a 40% solution of 3,4,5-trifluorophenylboronic acid in tetrahydrofuran from preliminary stage a) with 121.6 g (0.304 mol) of a 10% sodium hydroxide solution and 19.7 g (0.124 mol) of 2-nitrochlorobenzene. The particular ligand was then added at room temperature, the mixture was stirred and the palladium(II) chloride was finally added. Subsequently, the reaction mixture was heated to 105° C. This established a pressure of approx. 3-4 bar. After about 12 hours of reaction time, the pressure vessel was decompressed to standard pressure and cooled to 30° C., and the reaction mixture was discharged. For workup, the reaction mixture was taken up in tert-butyl methyl ether, the phases were separated and the aqueous phase re-extracted twice with tert-butyl methyl ether. The solvents were distilled off completely under reduced pressure, the final weight was determined and the content of the crude 3,4,5-trifluoro-2'-nitrobiphenyl was analyzed by means of quantitative HPLC. If desired, the crude 3,4,5-trifluoro-2'-nitrobiphenyl can be purified further, for example by crystallization from isobutanol.

After crystallization from isobutanol, the pure 3,4,5-trifluoro-2'-nitrobiphenyl is obtained with a melting point of 79° C.

| Ex. | Ligand | Mol % of $PdCl_2$ | Mol % of ligand | $PdCl_2$:ligand ratio | Yield | Mol % of 3,4,5-trifluorobenzene |
|---|---|---|---|---|---|---|
| b)-1 | triphenylphosphine | 0.48 | 4.8 | 1:10 | 86% | 12 |
| b)-2 | 1,3-bis(diphenyl-phosphinyl)propane | 0.26 | 0.26 | 1:1 | 9% | 29 |
| b)-3 | 1,3-bis(diphenyl-phosphinyl)-2,2-dimethylpropane | 0.26 | 0.26 | 1:1 | 97% | 2 |
| b)-4 | 1,3-bis(diphenyl-phosphinyl)-2-ethyl-2-butylpropane | 0.26 | 0.26 | 1:1 | 96% | 2 |

The molar percentages of PdCl$_2$ and ligand are each based on 3,4,5-trifluorophenylboronic acid.

The invention claimed is:
1. 3,4,5-Trifluoro-2'-nitrobiphenyl.

* * * * *